US 7,578,831 B2

(12) United States Patent
von Oepen et al.

(10) Patent No.: US 7,578,831 B2
(45) Date of Patent: Aug. 25, 2009

(54) BALLOON CATHETER

(75) Inventors: Randolf von Oepen, Los Altos Hills, CA (US); Lorcan Coffey, Tubingen (DE); Thomas Rieth, Hirrlingen (DE); Travis R. Yribarren, San Mateo, CA (US); Arik Zucker, Zurich (CH)

(73) Assignee: Abbott Laboratories, Abbott Park, IL (US)

( * ) Notice: Subject to any disclaimer, the term of this patent is extended or adjusted under 35 U.S.C. 154(b) by 293 days.

(21) Appl. No.: 11/474,111

(22) Filed: Jun. 23, 2006

(65) Prior Publication Data

US 2007/0016241 A1 Jan. 18, 2007

Related U.S. Application Data

(60) Provisional application No. 60/693,859, filed on Jun. 24, 2005, provisional application No. 60/742,765, filed on Dec. 5, 2005.

(51) Int. Cl.
*A61M 29/00* (2006.01)
(52) U.S. Cl. .................................... 606/194
(58) Field of Classification Search .............. 604/96.01, 604/101.01, 101.03, 103.04, 103.06–103.08; 606/191, 192, 194
See application file for complete search history.

(56) References Cited

U.S. PATENT DOCUMENTS 5,505,702 A    4/1996    Arney (Continued)

FOREIGN PATENT DOCUMENTS

EP    1 031 328 A1    8/2000

(Continued)

OTHER PUBLICATIONS

Partial International Search Report dated Feb. 19, 2007 from corresponding International Application No. PCT/US2006/024512.

(Continued)

*Primary Examiner*—Nicholas D Lucchesi
*Assistant Examiner*—Theodore J Stigell
(74) *Attorney, Agent, or Firm*—Fulwider Patton LLP

(57) ABSTRACT

A catheter arrangement is described that is arranged to permit a guide wire or other structure to be fed laterally from the region of an expandable working element. The catheter includes an elongate flexible tubular member and an inflatable structure carried by a distal portion of the flexible tubular member. The flexible tubular member has a guide wire lumen and at least one fluid supply lumen that is in fluid communication with the inflatable structure. The inflatable structure includes at least one, and preferably two, inflatable members (which may take the form of balloons). In the case of two inflatable members, the first and second inflatable members are radially spaced about the guide wire lumen such that at least one gap is formed between the inflatable members. With this arrangement, the distal end of a guide wire may be advanced through the guide lumen and out of a side opening such that the guide wire passes laterally between the first and second inflatable members. With such an arrangement, a guide wire passing out of the side opening in the region between the inflatable members can readily be directed into a second branch of a vessel bifurcation while the device is positioned in a first branch.

9 Claims, 12 Drawing Sheets

U.S. PATENT DOCUMENTS

| | | | |
|---|---|---|---|
| 5,549,555 A * | 8/1996 | Sohn | 604/101.01 |
| 5,947,977 A * | 9/1999 | Slepian et al. | 606/108 |
| 6,086,557 A * | 7/2000 | Morejohn et al. | 604/96.01 |
| 2003/0009209 A1 | 1/2003 | Hojeibane | |
| 2004/0015231 A1 * | 1/2004 | Suhr | 623/1.35 |
| 2006/0025843 A1 * | 2/2006 | Gurm et al. | 623/1.11 |

FOREIGN PATENT DOCUMENTS

| | | |
|---|---|---|
| WO | WO 96/34580 | 11/1996 |
| WO | WO 00/44307 | 8/2000 |

OTHER PUBLICATIONS

International Search Report dated May 23, 2007 from corresponding International Application No. PCT/US2006/024512.

Written Opinion dated May 23, 2007 from corresponding International Application No. PCT/US2006/024512.

* cited by examiner

BALLOON CATHETER

CROSS-REFERENCE TO RELATED APPLICATIONS

This application claims priority to U.S. Provisional Patent Application No. 60/693,859 filed Jun. 24, 2005 entitled "BALLOON CATHETER" and U.S. Provisional Patent Application No. 60/742,765 filed Dec. 5, 2005 entitled "CATHETER BALLOON DEVICE WITH INTERNAL GUIDEWIRE LUMEN AND METHOD OF FORMATION" both of which are herein incorporated by reference.

BACKGROUND OF THE INVENTION

The present invention relates generally to catheters. More particularly, the present invention relates to catheters that are designed to permit a guide wire or other structure to be fed laterally from the region of an expandable working element. Such arrangements are believed to be particularly useful in devices that are intended for use in the vicinity of vessel bifurcations.

Catheters are used in a very wide variety of medical procedures. Typically catheters are relatively long and flexible. Many times, (as for example in many vascular applications) the catheter may need to be inserted into a relatively tortuous vessel. Since it can be difficult to steer many types of catheters, guide wires are often used to position the catheters. Guide wires are typically formed from a very small diameter wire having a flexible tip that may be bent (typically pre-bent) by a physician to facilitate "steering" the guide wire to a desired location through a potentially tortuous path such as the vasculature.

In some applications the targeted region of a vessel may be at a location where the vessel bifurcates. For example, in cases where atherosclerotic plaque has developed in the region of a vascular vessel bifurcation, it may be desirable to perform a therapeutic treatment on the affected vessels. For example, in some applications, it may be desirable to stent one or both branches of a vessel bifurcation. In other applications, it may be desirable to perform an operation such as angioplasty or atherectomy in one branch, while stenting the other branch. In many such applications, it may be desirable to be able to position guidewires in both the main and the side branch of the bifurcation or to position a wire in the side branch when a balloon is already inserted into the main branch.

In situations where the main or side branch has been stented and the stent is positioned over the bifurcation it might be difficult to pass a wire through the stent structure for treating the other vessel, if desired. This is due, in part, to the fact that the angle between the two branches can be relatively large. In most bifurcations the vessels branch at a bifurcation angle of less than 60 degrees, but there are also vessel bifurcations in which the bifurcation angles are in the range of 60-90 degrees and sometimes even greater. Especially in cases where the bifurcation angle is greater than 60 degrees it can be difficult to pass a stent after implantation.

When treating a bifurcation it is important for the physician to be able to easily access the second vessel. Depending on the nature of the stenosis it might be possible that plaque shifting occurs during the treatment. This can occur when one of the vessels is dilated with a balloon or a stent is placed. Plaque shifting (which is sometimes referred to as the "snowplow effect" may then occlude (or partially occlude) the other vessel. To re-open the vessel, first a guide wire has to be placed in the second vessel. Depending on the lesion, the physician might decide to dilate the second vessel with a balloon catheter or place another stent.

Although there are currently a number of devices that are designed for use in the region of vessel bifurcations, there are continuing efforts to provide improved mechanisms for positioning a guidewire and/or appropriate working devices in the non-treated vessel of a bifurcation.

SUMMARY OF THE INVENTION

The present invention provides an inflatable working element for use with a delivery catheter device or the like. Typically, the catheter device includes an elongated flexible tubular member containing at least an inflation lumen and a main guidewire lumen. The working element includes a hollow balloon or bladder device selectively inflatable from a first condition to an expanded second condition. The bladder device defines an inflation passage extending from a proximal end opening to a distal end opening thereof. The proximal end opening is configured to cooperate with a distal portion of the elongated tubular member such the inflation passage is in flow communication with the shaft inflation lumen. The working element further includes a tubular arm member configured to be disposed in the inflation passage. The arm member includes a first end port accessible through the proximal end opening of the bladder device and an opposed second end port integrally formed with, and terminating at, a sidewall of the bladder device.

Accordingly, a secondary guidewire lumen is formed from the tubular arm member that is accessible through the inflation passage of the working element and which exits the sidewall of the bladder device. Moreover, the secondary guidewire lumen is fully accessible and operational while the bladder device is in its inflated condition. This enables the positioning of both a main guidewire and of a second guidewire through the secondary guidewire lumen without disturbing the operation of the working element. Such access is extremely advantageous to enable access to a side branch of a bifurcated vessel.

In another aspect of the present invention, method of fabricating an inflatable balloon element is disclosed for a catheter device suitable for treating a vessel bifurcation. The method of formation includes forming a one-piece balloon element having a hollow body portion defining an inflation passage extending from a proximal end opening to a distal end opening thereof. The body portion includes a flexible tubular arm member having a first end defining a first end port directed generally radially away from the body portion of the balloon element, and an opposed second end integrally formed in a sidewall of the body portion. The second end defines a second end port that terminates at the body portion inflation passage such that the second end port is in direct access communication with the inflation passage. The method further includes inverting the tubular arm member inside out such that the arm member is disposed in the inflation passage, and having the first end port accessible through the proximal end opening of the bladder device and the opposed second end terminating at the sidewall in a manner such that the second end port is out of direct access communication with the inflation passage.

In one specific embodiment, the method includes mounting the proximal end of the balloon element to a distal portion of an elongated shaft of the catheter device such the inflation passage of the balloon element is in flow communication with an inflation lumen of the catheter elongated shaft.

In another arrangement, the forming includes molding the hollow body portion and the arm member about a balloon mold device configured in a predetermined shape. In still another specific embodiment, the forming includes electrografting the hollow body portion and the arm member about a balloon mold device configured in a predetermined shape.

In still another aspect of the present invention, a catheter device is provided including an elongated flexible tubular shaft containing an inflation lumen and a main guidewire lumen therethrough. An inflatable working element is mounted to the flexible tubular shaft, and includes a hollow bladder portion selectively inflatable from a first condition to an expanded second condition. The bladder portion defines an inflation passage extending from a proximal end opening to a distal end opening thereof. The proximal end opening is configured to cooperate with a portion of the elongated shaft such that the inflation passage is in access communication with the shaft inflation lumen. The working element further includes a tubular arm member configured to be disposed in the inflation passage. A first end port of the arm member is accessible through the proximal end opening of the bladder portion and an opposed second end port integrally formed with, and terminating at, a sidewall of the bladder portion.

To achieve the foregoing and other objects of the invention a catheter arrangement is described that is arranged to permit a guide wire or other structure to be fed laterally from the region of an expandable working element. In one embodiment of the invention a catheter that is sized suitably for insertion in a body vessel is described. The catheter includes an elongate flexible tubular member and an inflatable structure carried by a distal portion of the flexible tubular member. The flexible tubular member has a guide wire lumen and at least one fluid supply lumen that is in fluid communication with the inflatable structure. The inflatable structure includes at least one, and preferably two, inflatable members (which may take the form of balloons). In the case of two inflatable members, the first and second inflatable members are radially spaced about the guide wire lumen such that at least one gap is formed between the inflatable members. With this arrangement, the distal end of a guide wire may be advanced through the guide lumen and out of a side opening such that the guide wire passes laterally between the first and second inflatable members. With such an arrangement, a guide wire passing out of the side opening in the region between the inflatable members can readily be directed into a second branch of a vessel bifurcation while the device is positioned in a first branch.

In some embodiments, a guide wire channel is provided that extends laterally from the guide wire lumen in a region between the inflatable members when the members are in an inflated position. The guide channel may be formed in a variety of ways. By way of example, when balloons are used as the inflatable members, the channel may be formed by attaching portions of the balloons together using adhesives, welding or adding a sleeve to define the channel. Alternatively, the channel may be formed from a separate piece or as an extension of a guide wire lumen.

In some embodiments a second guide wire lumen may be provided. In one such embodiment, the distal end of the second guide wire lumen is bent up such that it extends into the gap between the inflatable members and opens to the side of the catheter. With such an arrangement, a guide wire passing out of the second guide wire lumen can readily be directed into the second branch of a vessel bifurcation while the device is positioned in the first branch.

In still other embodiments, more than one side opening may be provided in the guide wire lumen to facilitate access at multiple locations along the inflatable structure. The additional side openings may be either radially or longitudinally spaced.

When desired, one or more retaining sheaths that surround the balloon segments may be provided to help insure that the overall balloon structure takes on a more tubular geometry when it is expanded.

BRIEF DESCRIPTION OF THE DRAWINGS

The invention, together with further objects and advantages thereof, may best be understood by reference to the following description taken in conjunction with the accompanying drawings in which.

It is to be understood that in the drawings, like reference numerals designate like structural elements. Also, it is understood that the depictions in the figures are diagrammatic and not to scale.

DETAILED DESCRIPTION OF THE PREFERRED EMBODIMENTS

The present invention relates generally to catheters that are designed to permit a guide wire or other structure to be fed laterally from the region of an expandable working element. Such arrangements are believed to be particularly useful in devices that are intended for use in the vicinity of vessel bifurcations.

Figure 1:
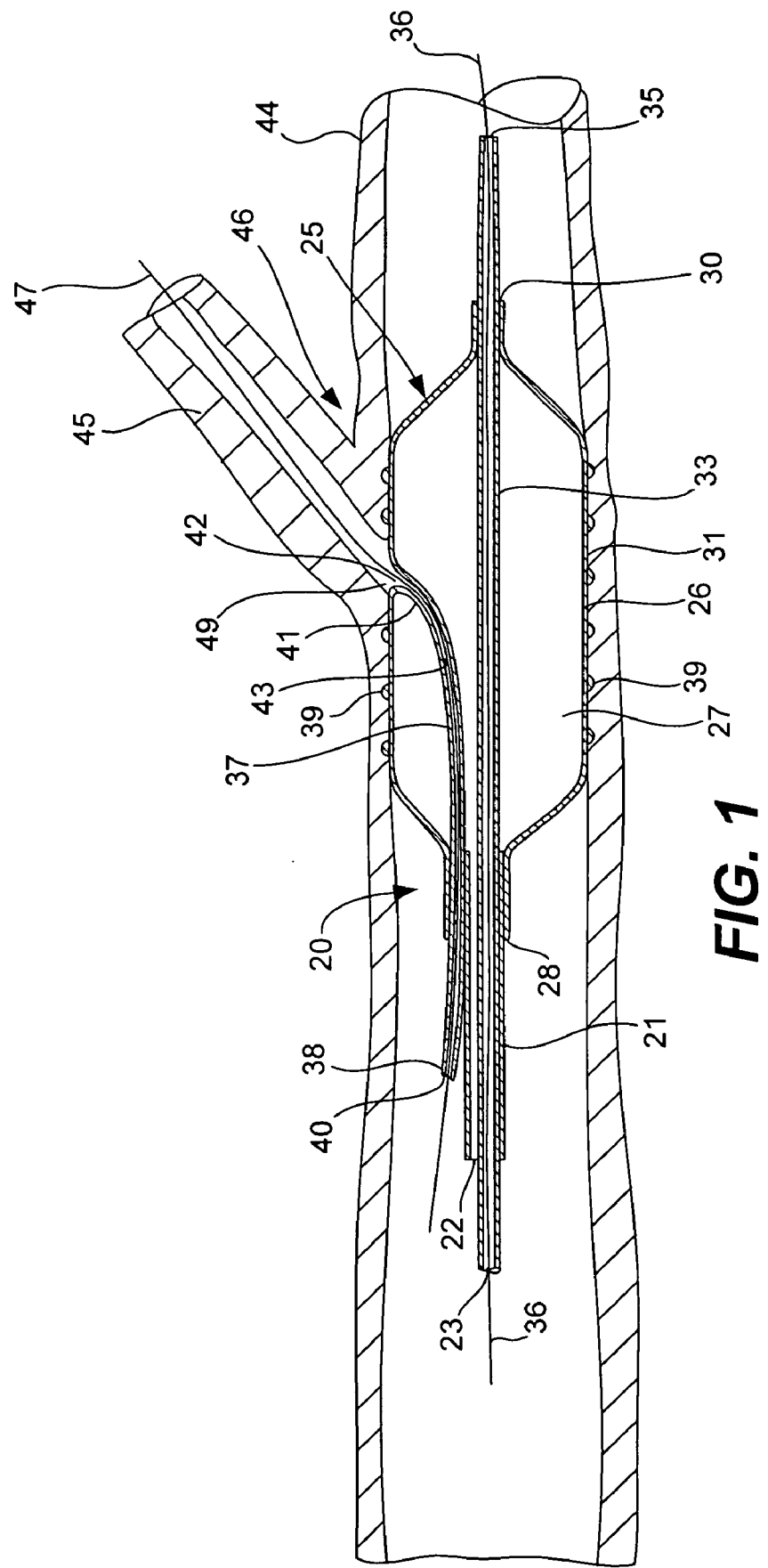
FIG. 1 is a fragmentary, side elevation view, in cross-section, of a catheter assembly constructed in accordance with the present invention, deployed in a bifurcated vessel.
Figure 2:
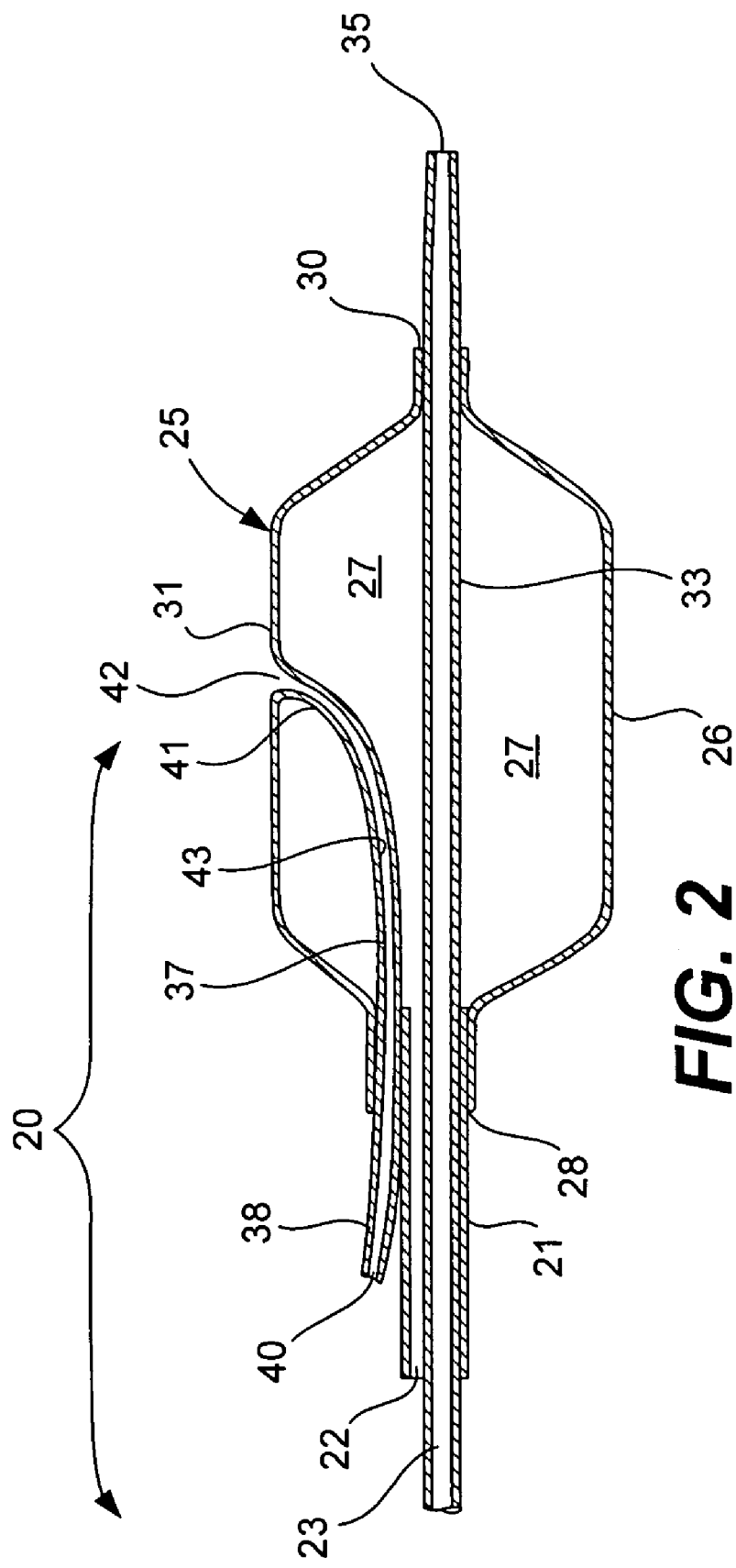
FIG. 2 is a fragmentary, side elevation view, in cross-section, of the catheter assembly of FIG. 1, illustrating a tubular arm member or an inflatable working element.
Figure 3:
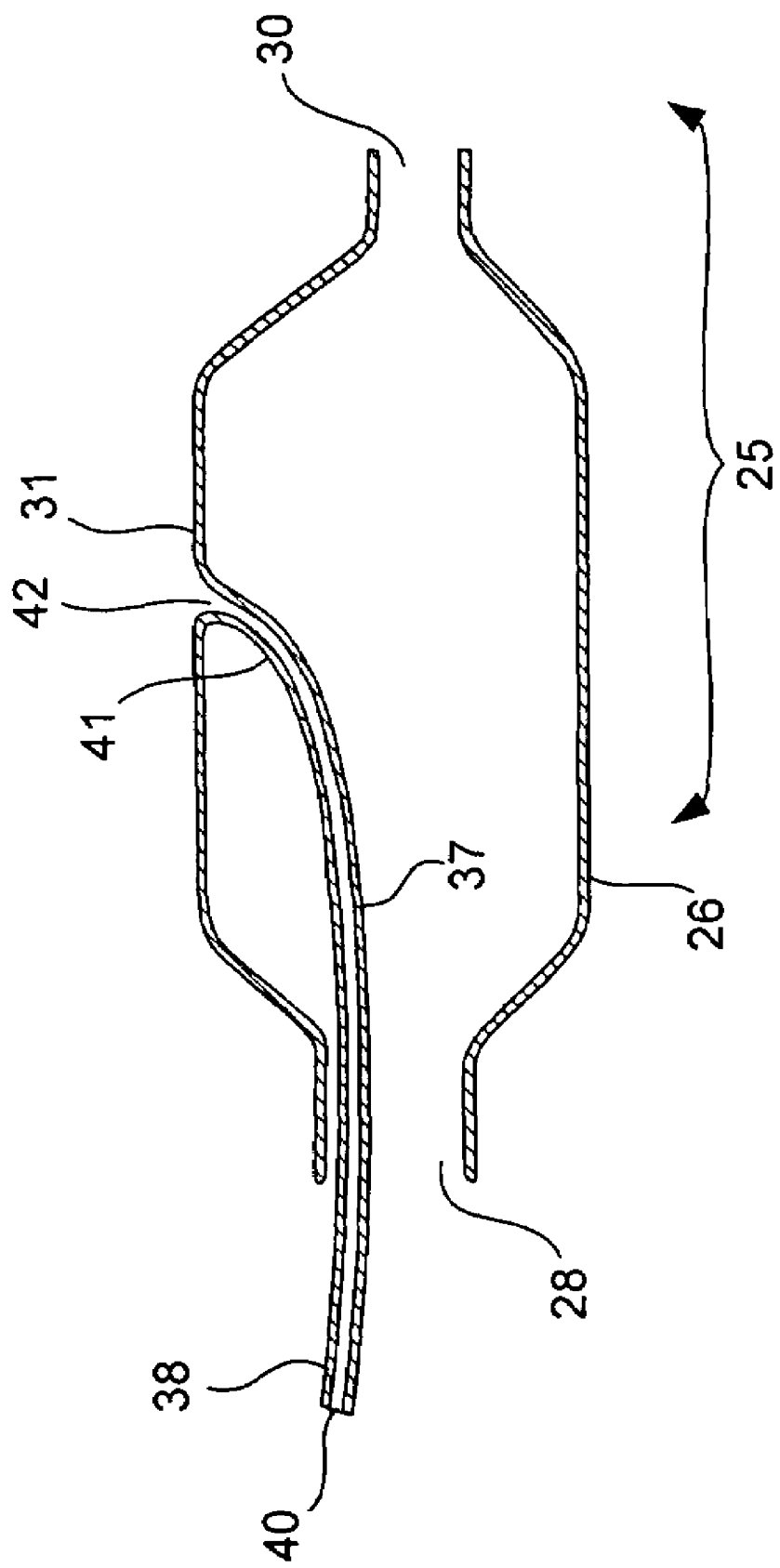
FIG. 3 is a side elevation view, in cross-section, of the inflatable working element of FIG. 2.

Referring now to FIGS. 1-3, a delivery catheter assembly, generally designated 20, is provided having an elongated tubular member or catheter shaft 21 that defines at least one inflation lumen 22 extending through the shaft. As will be appreciated by those familiar with the art, only the distal, working end of the catheter assembly 20 is shown in these figures for illustrative purposes. The length and size of the catheter shaft 21 will typically depend on its desired application and the proximal end (not shown) of the catheter would typically be outfitted with a suitable handle and ports, valves and other structures for controlling the working (distal) end of the catheter.

The delivery catheter assembly 20 is particularly suitable for deployment in vascular vessels including coronary vessels. However, in other embodiments, the catheter may be designed for insertion in any body vessel or tubular structure of the body. The flexible catheter shaft 21 may include any suitable number of lumens. In the illustrated embodiment, the lumens include at least a main guidewire lumen 23 and inflation (e.g., fluid supply) lumen 22.

Mounted to a distal portion of the catheter shaft 21 is a one-piece inflatable working element 25 of the catheter assembly 20. The working element 25 contains a substantially cylindrical hollow bladder portion 26 defining an inflation passage 27 extending longitudinally therethrough from a proximal end opening 28 to a distal end opening 30. The hollow bladder portion includes a substantially thin sidewall 31 with a substantially cylindrical exterior surface and an opposed interior surface. A proximal portion of the working element 25 tapers radially inward toward the proximal end opening 28, as does a distal portion of the working element 25 that tapers radially inward toward the distal end opening 30.

Similar to most conventional inflatable balloon catheter designs, the proximal end opening 28 and the distal end opening 30 are sized to mount and seal to respective portions of the elongated catheter shaft 21 of the catheter assembly, while the substantially thin and flexible central bladder portion 26 is configured for selective inflation from an unexpanded first condition to an expanded second condition (FIG. 1). Hence, the transverse cross-sectional dimension of the inflation passage 27, in the expanded second condition, is significantly greater than that of the inwardly tapered end portions of proximal end opening 28 and the distal end opening 30.

When the inflatable working element 25 is mounted to the flexible catheter shaft 21, the inflation lumen 22 of the catheter shaft is in flow communication with the inflation passage 27 of the working element 25. Accordingly, by operating the control systems at the proximal end of the catheter assembly, the central bladder portion 26 of the working element 25 can be selectively inflated from the first condition to the inflated second condition.

A distal tube portion or extension 33 of the flexible catheter shaft 21 extends through the inflation passage 27 of the inflatable working element 25, where a distal end of the catheter assembly 20 terminates just past the distal end opening 30 of the working element. As best shown in FIG. 2, the catheter shaft distal tube portion 33 extends longitudinally through the working element 25, and defines the distal portion of the main guidewire lumen 23 where it terminates at a distal port 35 at a distal end of the catheter shaft 21. Hence, a main guidewire 36 may extend through the main guidewire lumen 23 of the catheter assembly 20, and out through the distal port 35 of the catheter distal end. This passage enables the catheter shaft 21 to be advanced along the main guidewire 36 that is strategically disposed in a vessel.

FIG. 2 best shows that the distal tube portion 33 defines at least a portion of the main guidewire lumen 23. For example, the distal tube portion 33 may simply extend from the distal end of the main portion of the catheter shaft 21, having at least one side integral therewith as shown in FIG. 3. In another configuration, the tube portion 33 may actually be contained within and extend through at least a portion of a larger lumen of the catheter shaft in a manner independent of the shaft.

Referring back to FIG. 1, an interior wall defining the distal end opening 30 of the working element 25 is configured to seal around the corresponding outward facing surface of the distal tube portion 33 in a fluid-tight manner. Similarly, a fluid-tight seal is formed between an interior wall defining the working element proximal end opening 28 and the corresponding exterior facing surface of the catheter shaft 21 and/or at least a portion of the distal tube portion 33. Collectively, these two seals isolate the main guidewire lumen 23 from the inflation passage 27 of the working element 25, and permit inflation of the element.

In accordance with the present invention, the working element 25 includes an inverted tubular arm member 37 integrally formed with the hollow bladder portion 26. The tubular arm member 37 include a first end 38 that defines a first end port 40, and an opposed second end 41, integrally formed and attached to the sidewall 31 of the hollow bladder portion 26, that defines a second end port 42. The tubular arm member 37 further includes a side lumen or secondary guidewire lumen 43 extending therethrough from the first end port 40 to the second end port 42.

In the inverted configuration of the tubular arm member 37, as shown FIG. 3, the tubular arm member 37 passes through the inflation passage 27 in the direction toward the proximal end opening 28. In one specific embodiment, the length of the arm member 37 is sufficient to position the first end 38 at least through and just beyond the proximal end opening 28 of the working element proximal portion. Accordingly, in the inverted state, the secondary guidewire lumen 43 is now essentially isolated from flow access to the inflation passage 27, and the second end port 42 is out of direct access communication with the working element inflation passage 27. Rather, the second end port 42 is in direct access communication with the exterior of the balloon or bladder portion 26 that enables access communication through the inflation lumen and out of the sidewall 31 of the bladder portion 26.

Both the main guidewire lumen 23 and the secondary guidewire lumen 43, hence, are formed that simultaneously permit passage through the inflation lumen 22 of the working element 25 without any disruption in operation thereof. In particular, the secondary guidewire lumen 43 provides easy access to a side branch vessel 45 of a bifurcated vessel 46 directly through the sidewall 31 of the working element bladder portion 26 (FIG. 1). This accessibility is possible even after inflation of the working element and deployment of a stent 39.

Once the catheter assembly 20 is manipulated along the main guidewire 36 until the working element 25 is at least partially disposed in the main vessel 44 of the bifurcated vessel 46, the second end port 42 is aligned with the opening 49 into the side branch vessel 45. Such alignment is maintained during inflation of the bladder portion 26 from the first condition to the inflated second condition, although constant alignment may not be necessary. Subsequently, a second guidewire 47 can be negotiated into secondary guidewire lumen 43 of the tubular arm member 37. Unlike the current systems, the working element 25 will not require deflation and removal of thereof prior to guidance of the tip of the second guidewire therethrough. Hence, since the inflated working element 25 remains inflated in the second condition, the tip of the second guidewire can be confidently navigated and negotiated through the working element 25, via the secondary guidewire lumen 43 of the tubular arm member 37, and out of the bladder portion sidewall 31, via second end port 42. Once past this juncture, the tip will be guided through the scaffolding of the deployed primary stent 39 and into the side branch vessel 45 of the bifurcated vessel 46. Such deployment and alignment of the second guidewire 47 to the side branch vessel 45, accordingly, is substantially simplified.

As best viewed in FIGS. 2 and 3, the transverse cross-sectional dimension of the secondary guidewire lumen 43 of the tubular arm member 37 is substantially smaller then both that of the inflation passage 27 and of the proximal end opening 28 of the working element 25. In general, the working element proximal end opening 28 must be sized to receive at least the distal tube portion 33 of the catheter shaft 21 upon which it is sealed and mounted to. In turn, the catheter shaft 21 must be sized to accommodate at least the main guidewire lumen 23 and the inflation lumen 22.

In one particular configuration shown in FIGS. 1 and 2, the first end 38 of the tubular arm member 37 is positioned between the catheter shaft 21 and the proximal portion of the working element 25 that defines the proximal end opening 28. As illustrated, the first end 38 of the tubular arm member 37 must be of sufficient length to pass through the proximal end opening 28 where the first end port 40 is accessible. The interior wall defining the distal end opening 30 of the working element 25 is sealed against the exterior surface of the catheter shaft and against the tubular arm member to properly isolate the inflation passage of the bladder portion 26.

The first end 38 of the tubular arm member 37 may be mounted to a tube device or the like (not shown) that enables access to the secondary guidewire lumen 43 at a position more proximal to the operating end of the catheter assembly. Such tube device may be internal or external to the catheter shaft 21. This will ease advancement of the second guidewire to the working element 25. In another configuration, as shown in FIG. 1, the secondary guidewire lumen 43 may just be accessible at the first end port 40 of the tubular arm member 37 just proximal to the working element 25. In still another configuration, the secondary guidewire lumen 43 of the tubular arm member 37 may enter the catheter shaft 21 and exit through a welded transition as in RX technology more proximal to the operating end of the catheter assembly.

Figure 4:
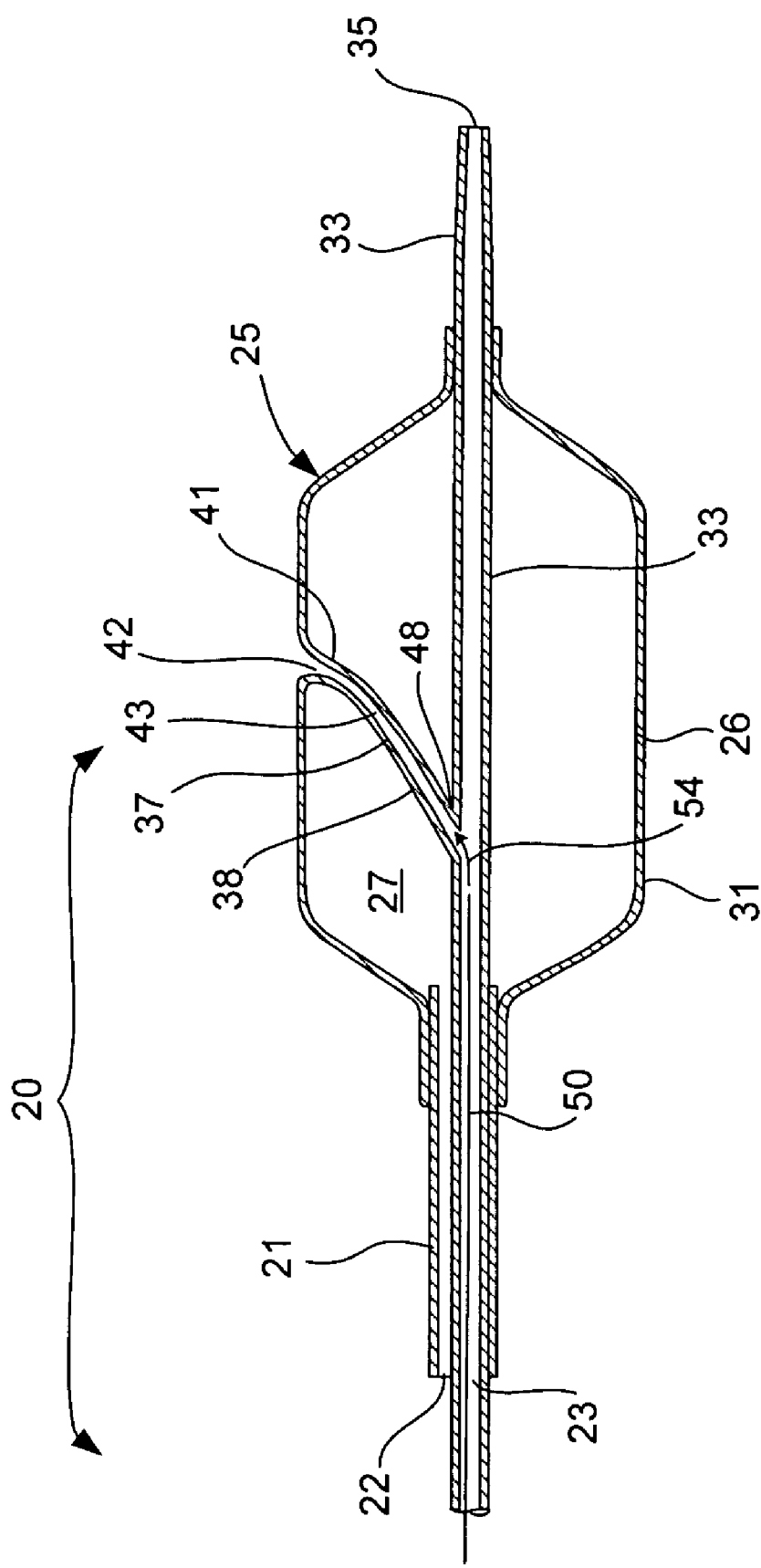
FIG. 4 is a fragmentary, side elevation view, in cross-section, of an alternative embodiment catheter assembly.

In either configuration, the second (side branch) guidewire 47 will seamlessly enter the secondary guidewire lumen 43 of the tubular arm member 37, via the first end 38. This permits the second guidewire 47 to pass through the inflation lumen 22 of an inflated working element 25, and out through the sidewall 31 thereof, via the tubular arm second end port 42, without requiring deflation or removal of the working element 25. In fact, as shown in FIG. 4, this design enables access to both the main and secondary guidewires through the inflated catheter balloon or working element at the treatment area. As mentioned, this is very advantageous in that the catheter assembly 20 need not be subsequently realigned with the side branch vessel 45 in order to negotiate the second guidewire 47 into the side branch vessel 45, as the current designs require. Another benefit includes not needing to switch wires within the anatomy, thereby reducing the risk of dissection. It will be appreciated that the guidewire may also be back loaded into the side lumen at the distal end.

In another configuration not shown, the first end 38 of the tubular arm member 37 may be sealably mounted to or communicate with structure contained internally within the catheter shaft 21 that defines a shaft secondary guidewire lumen. It will be appreciated, however, that such a sealed mount to this secondary guidewire structure of the catheter shaft could also be performed inside the working element inflation passage 27 as well. In fact, in the embodiment illustrated in FIG. 4, the first end 38 of the tubular arm member 37 can be configured to communicably intersect the main guidewire lumen 23 within the inflation passage 27 of the working element 25. This communication intersection 48 between the arm member secondary guidewire lumen 43 and the main guidewire lumen 23, which incidentally can also occur outside of the inflation passage 27, permits access communication with both lumens from a single main guidewire lumen 23 of the catheter shaft 21.

This arrangement is beneficial in that the entire treatment of the bifurcated vessel 46 may be performed using a single guidewire 50. For example, once the catheter is aligned and the working element 25 is inflated to deploy the stent 39, then the single guidewire 50 can be retracted until the distal tip thereof is just proximal to the communication intersection 48. Subsequently, the distal tip of the single guidewire 50 is oriented and navigated into and through the secondary guidewire lumen 43 (along the path of arrow 54 in FIG. 4). After passing through the second end port 42, the guidewire is passed through the stent scaffolding and into the side branch vessel 45.

After the working element 25 is deflated, the catheter shaft 21 can be withdrawn along the guidewire 50 while retaining the distal tip thereof in the side branch vessel 45. Subsequently, another catheter can be positioned along the same guidewire 50, and into the side branch vessel 45 to complete the procedure.

Figure 5:
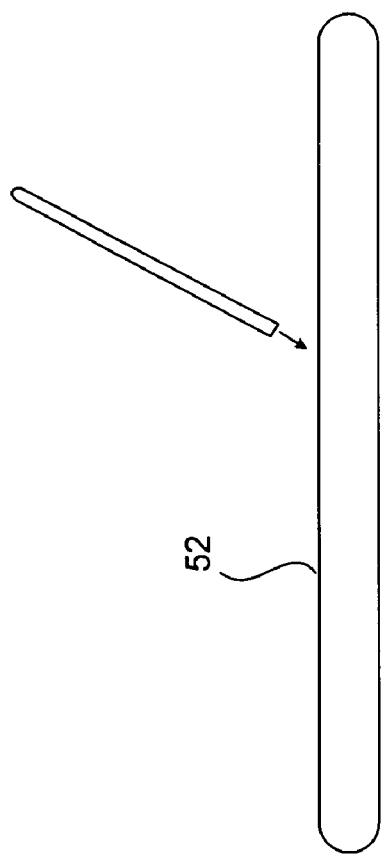
FIG. 5 is a side elevation view of a balloon mold constructed in accordance with the present invention.
Figure 6:
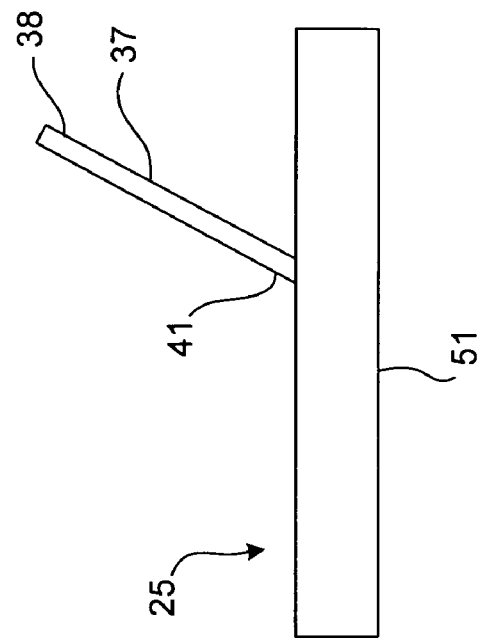
FIG. 6 is a side elevation view of an initial cylindrical shell body formed from the balloon mold of FIG. 5.

In accordance with another aspect, the present invention includes a technique of fabrication of the inflatable working element 25 with the tubular arm member 37. As best illustrated in FIGS. 5 and 6, in one embodiment, the working element 25 is initially formed using a balloon mold 52 having a substantially cylindrical shape. The balloon mold 52, as will be described, is applied using conventional injection molding, dip molding, blow molding, electrograft techniques, or bonding of individual tubings using welding or solvent bonding techniques, to fabricate a substantially cylindrical shell-shaped mold body containing the proximal end opening 28 and the distal end opening 30.

To form the tubular arm member 37, a removable core pin 53, having the desired diameter for the secondary guidewire lumen 43, is positioned into a hole (not shown) in the side of the balloon mold 52. The location and position of the core pin 53 is, of course, pre-selected so as to properly position the second end port 42 at the desired location relative bladder portion 26. Moreover, the angle and direction of the core pin 53 are pre-selected so as to properly angle and position the tubular arm member 37 in the desired direction. The removable core pin, for example, is preferably angled relative a longitudinal axis of the cylindrical shell body 51 in the range of about 20° to about 90°, and most preferably about 60°. Further, while the core pin may be substantially linear and uniform in diameter, it will be appreciated that the core pin may also be curvilinear and/or non-uniform in diameter, as long as the core pin can be removed from the tubular arm member without jeopardizing the integrity thereof.

In accordance with the present invention, however, the tubular arm member 37 must be integrally fabricated into the cylindrical shell body 51. This is performed by inserting a removable core pin 53, having the desired diameter for the secondary guidewire lumen 43, into a hole in the side of the balloon mold 52. The insertion of the core pin 53, of course, is to be at a pre-selected location so as to properly position the second end port 42 as the desired location. Further, the orientation of the core pin, relative to the balloon mold 52, is retained at a pre-selected angle and direction. The removable core pin, for example, is angled relative a longitudinal axis of the balloon mold 52 in the range of about 20° to about 90°, and most preferably about 60°. Further, while the core pin may be substantially linear and uniform in diameter, it will be appreciated that the core pin may also be curvilinear and/or non-uniform in diameter, as long as the core pin can be removed from the tubular arm member 37 without jeopardizing the integrity thereof.

After initial molding or electrografting of the cylindrical shell body 51 and the tubular arm member 37 using conventional molding techniques, the core pin 53 is removed from the cylindrical balloon mold 52, leaving the tubular arm member 37 in tact with the cylindrical shell body 51. Subsequently, the cylindrical shell body 51 is removed from of the balloon mold 52 leaving the initial cylindrical shape of the working element 25, as shown in FIG. 6.

To function in accordance with the present invention, the tubular arm member 37 must be in an inverted configuration (FIG. 3) relative to the initial molded configuration of the cylindrical shell body 51 (FIG. 6). Briefly, it will be appreciated that the inverted state of the tubular arm member is a relative term in that, as will be described below, this configuration can accomplished by either inverting the tubular arm member 37 itself inside out or inverting the hollow bladder portion 26 inside out. For example, in the latter case, an elongated tool 58 or the like with a plurality of pronged ends 60 can be passed through the inflation passage 27 of the working element. Using the pronged ends 60, as shown FIG. 7, either the proximal end or the distal end of the working element 25 can be engaged and pulled longitudinally through the center thereof. Hence, in this technique, the bladder portion 26 is inverted rather than the much smaller diameter tubular arm member 37. It will be understood, however, that the tubular arm member 37 could be inverted using this same technique without departing from the true spirit and nature of the present invention. It will further be appreciated that the inversion can occur either when the working element is in its initial cylindrical shell body 51 or in the final expanded shape of FIG. 9, as will be described.

Figure 8:
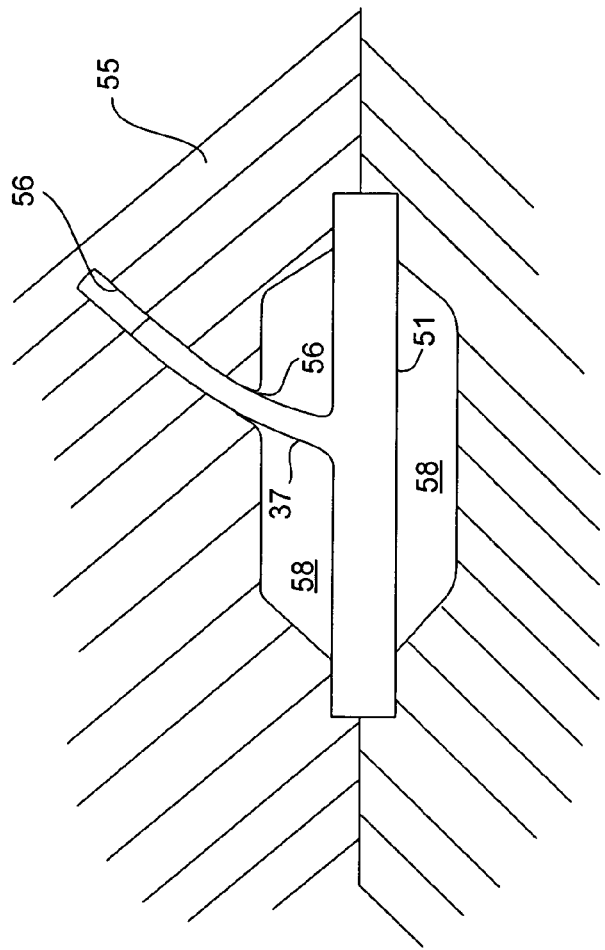
FIG. 8 is a fragmentary, side elevation view, in cross-section, of a mold shell with the initial cylindrical shell body of FIG. 6, before deformation to its final shape of FIG. 7.
Figure 7:
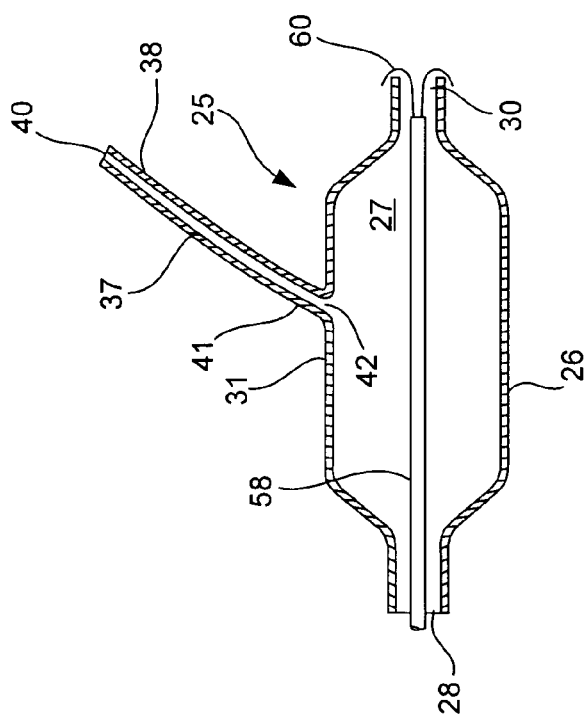
FIG. 7 is a side elevation view, in cross-section, of an inflatable working element being inverted through a tool device.

To further radially expand the cylindrical shell body 51, forming the final working element shape of FIG. 3 or 7 having the inwardly tapered proximal and distal ends, a mold shell 55 (FIG. 8) is employed. This mold shell 55 includes an interior cavity 57 having a shape substantially similar to the desired final shape of the working element 25 where the central bladder portion 26 has a diameter greater than the distal and proximal ends.

To accommodate for the tubular arm member 37 of the initial shape of the working element (i.e., cylindrical shell body 51), the mold shell 55 may include a strategically placed side port 56 that is sized and formed for receipt of the arm member therein. Once the cylindrical shell body 51 is placed in the cavity 57 of the mold shell 55, and the tubular arm member 37 is aligned with, and received in, the side port 56, the inflation passage 27 is pressurized. By heating the pressurized cylindrical shell body 51, the working element 25 will be permanently deformed from its initial molded shape into its operational shape of FIG. 3 or 7. By way of example, for a balloon catheter element composed of nylon, it may be heated in a range of about 60° C. to about 120° C. with an internal pressure in the range of about 20 Bar to about 40 Bar. It will of course be appreciated that other heats and pressure combinations may apply.

Effectively, during the formation of the bladder portion 26, the internal pressurization of the working element causes the walls to expand and deform radially outwardly until the sidewall 31 of the bladder portion 26 contact the interior walls of the mold shell cavity 57. These deformed sidewalls 31 are uniformly thinned, compared to the walls of the proximal and distal portions, as they are deformed into a larger diameter. Subsequently, in this configuration, the bladder portion 26 or the tubular arm member 37 would then be inverted using one of the techniques above-mentioned.

Alternatively, the initially molded working element can be inverted first, and then deformed using the mold shell 55. In this embodiment, the side port 56 of the mold shell 55 will of course not be required since the inverted tubular arm member 37 will not require accommodation on the exterior of the working element. The second guidewire lumen 43 of the tubular arm member 37, however, will need to be blocked so as to enable pressurization of the inflation passage 27. This temporary blockage can be anywhere along the tubular arm member such as near the second end port 42.

In accordance with FIGS. 9-14 there is shown and described below an alternative embodiment of a catheter in accordance with the present invention, wherein the catheter in accordance with the present invention addresses those problems as described above in a similar manner utilizing alternative construction thereof.

Figure 9:
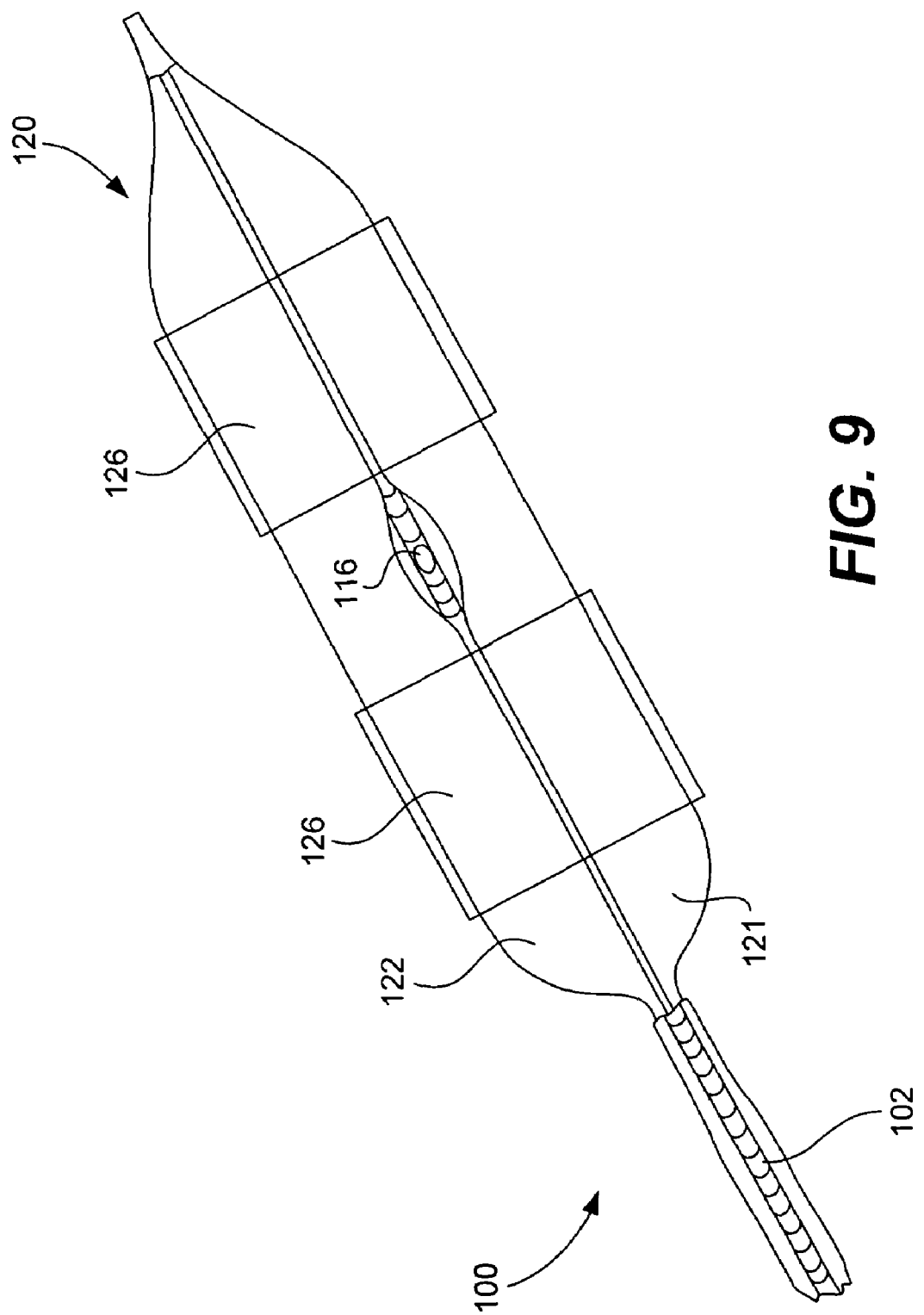
FIG. 9 is a diagrammatic side view of the distal region of a catheter formed in accordance with one embodiment of the present invention.
Figure 10:
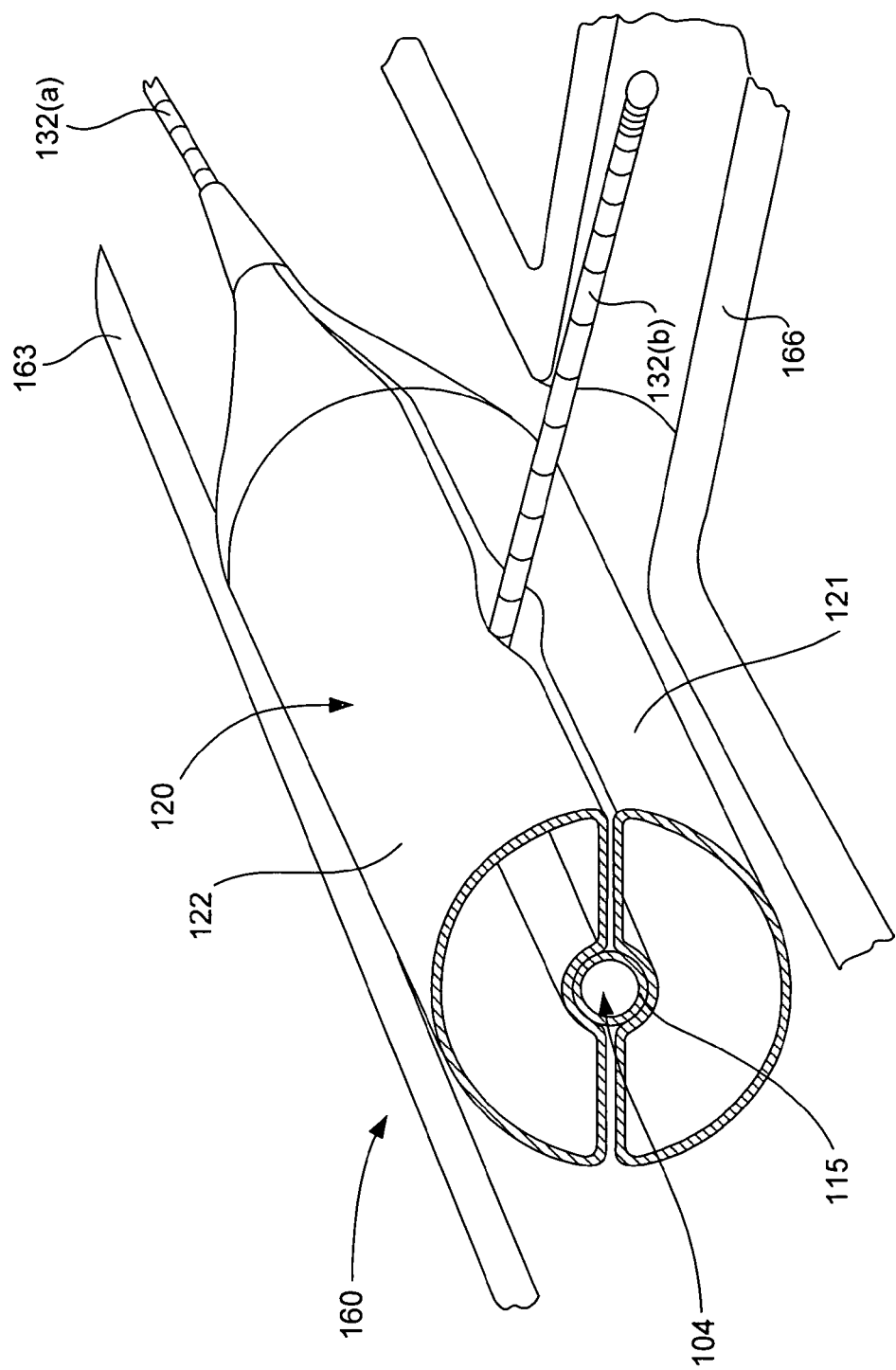
FIG. 10 is a diagrammatic perspective view of a portion of a distal segment of a catheter formed in accordance with another embodiment of the present invention illustrating a representative placement at a vessel bifurcation.
Figure 11:
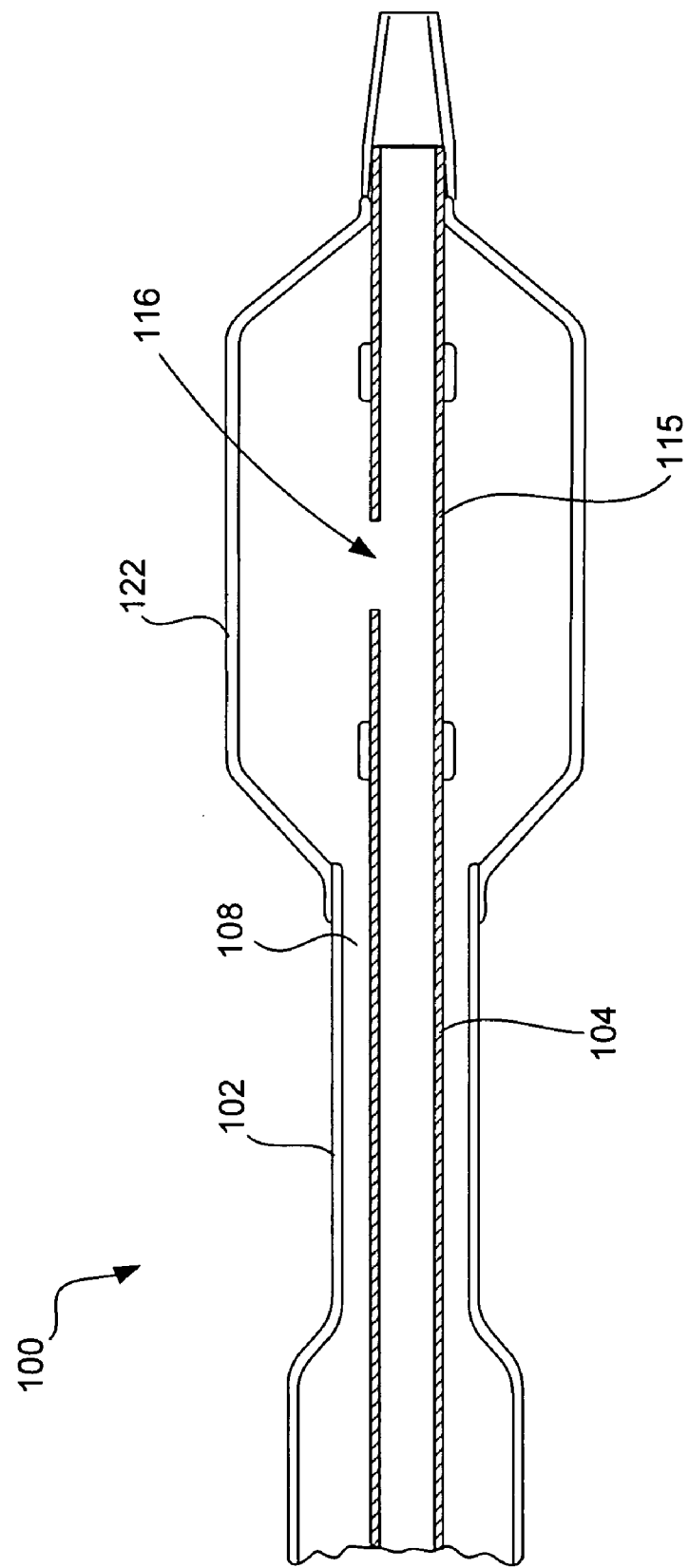
FIG. 11 is a longitudinal cross section view of the distal region of a catheter formed in accordance with another embodiment of the present invention.

FIGS. 9-11 are diagrammatic views of a balloon catheter that will be used to introduce some of the concepts that are included in various embodiments of the present invention. A catheter 100 has an elongated flexible tubular member 102 that is sized suitably for insertion in a vessel of interest. As will be appreciated by those familiar with the art, only the distal, working end of the catheter 100 is shown in these figures. The length and size of the catheter 100 will typically depend on its desired application and the proximal end of the catheter would typically be outfitted with a suitable handle and ports, valves and other structures for controlling the working (distal) end of the catheter.

In the described embodiment, the catheter is designed for deployment in vascular vessels including coronary vessels. However, in other embodiments, the catheter may be designed for insertion in any body vessel or tubular structure of the body. The flexible tubular member 102 may include any suitable number of lumens. In the illustrated embodiment, the lumens include guide wire lumen 104 and inflation (e.g., fluid supply) lumen 108. A guide tube segment 115 of the flexible tubular member 102 that includes the guide wire lumen 104 extends beyond the end of the fluid supply lumens 108.

An inflatable structure 120 that includes a pair of inflatable member 121, 122 is mounted near the distal end of the catheter. In the illustrated embodiment, the inflatable structures take the form of balloons. The fluid supply lumen(s) 108 open into the balloons 121, 122 to facilitate inflation of the balloons. Each inflatable balloon is in fluid communication with a fluid supply lumen. The balloons may be coupled to the same fluid supply lumen so that they are inflated simultaneously or they may be coupled to different fluid supply lumens so that they may optionally be inflated independently.

As best seen in FIG. 10, the balloons 121 and 122 are radially spaced with respect to one another. Each balloon is adhered to a portion of the guide tube segment 115. In the illustrated arrangement, when the balloons are inflated, the balloons take a substantially semicircular or "D-shaped" lateral cross-sectional profile and each occupy close to a 180 degree radial segment of the inflatable structure 120. The balloons are positioned back to back so that together, they extend most of the way around the guidewire lumen. Thus, the illustrated inflatable structure 120 is sometimes referred to herein as a Double-D balloon design. However, in other embodiments, radial gaps of various sizes may be provided between the balloons.

In the embodiment illustrated in FIG. 10, the guide wire lumen 104 extends beyond the fluid supply lumens 108. In this embodiment, the balloons may be attached to the flexible tubular member/guide wire lumen at any appropriate position, as for example along the length of the balloons, at their distal and proximal ends or the like. The balloons may be attached by any suitable mechanism, as for example, by an adhesive, welding, ultrasonic welding, rotation welding, RF energy, laser welding, white light welding, or mechanical bonding.

As pointed out above, the embodiment shown in FIG. 10 include a guide tube segment 115 that supports the balloons 121, 122. However, in other embodiments, the guide tube segment may be eliminated so that the guide wire lumen is effectively free floating between the balloons. In such an arrangement, the proximal and distal ends of the inflatable structure 120 could be secured together to provide the desired structure.

It should be appreciated that in many medical applications (e.g., most stent delivery and angioplasty applications) it is generally desirable to provide an inflatable structure that has relatively uniform expansion in all directions. At the same time, most balloons are designed in a way such that when inflated in an unconstrained state, they naturally take on a substantially circular cross sectional profile, as opposed to a D-shaped profile. However, as will be described in more detail below, various sheaths and other arrangements can be used to encourage the individual balloons to adopt a profile that is closer to the illustrated shape than an ordinary balloon might naturally adopt. Thus, the overall shape of the balloon structure takes on a substantially circular cross-sectional profile.

In the illustrated embodiment, and in most designs, the balloons 121, 122 are positioned so that they match longitudinally (i.e., so that their respective ends are at nearly the same longitudinal position). Although this is not a requirement, in most embodiments such an arrangement is preferred.

The guide tube segment 115 (i.e., the guide wire lumen) has an opening 116 (best shown in FIGS. 1 and 3) which opens into a region that is radially between multiple balloons 121, 122. With this arrangement, a guide wire 132 (or other suitable device) that passes through the guide wire lumen 104 can be passed through the opening 116 so that it exits laterally from the catheter in a region between the adjacent balloons 121, 122 as best illustrated in FIG. 10. This type of arrangement can be particularly useful when attempting to place a guide wire (or other structure) in a branch 166 of a bifurcated vessel 160 while the distal tip of the catheter is positioned in the other branch 163 of the bifurcation.

In the embodiments illustrated in FIGS. 9-11, a single side opening 116 is provided in the guide tube lumen. However, in other embodiments a variety of other arrangements and structures may be used. For example, more than one side openings 116 may be provided in the guide tube segment. Depending on the needs of a particular application, the side openings may be longitudinally and/or radially spaced relative to one another. For example, if it is desirable to be able to deploy the guide wire (or other structure) laterally in two different directions relative to the catheter, a pair of angularly (radially) offset openings (e.g., openings that are radially offset by 180 degrees) may be provided in the guide tube segment 115 with each opening being arranged to open into a different gap between the balloons 121, 122. In another example, a plurality of longitudinally spaced openings may be provided in the guide tube segment in order to permit lateral access at multiple locations along the catheter. This can be particularly useful in embodiments that incorporate elongated balloon structures. In addition, more than two individual balloons can be used to create three or more radial gaps in the overall inflatable structure 120.

To illustrate some of the advantages of the described arrangement, it is helpful to consider a few possible uses of the described catheter. By way of example, in one application, a guide wire 132 may be inserted into a vessel 160 of interest continuing past a targeted bifurcation in the main branch 163 of the vessel. A catheter 100 having a working end that includes the Double-D balloon design 120 is then inserted over the guide wire and is positioned in the vessel so that the working elements (which include the inflatable structure 120) is positioned in a region adjacent the targeted bifurcation with the opening 116 in the guide tube segment 115 facing generally towards the side branch 166. With the catheter remaining in place, a guide wire may then be inserted into the side branch 166 by feeding the guide wire through the opening 116. The guide wire 132 may be fed into the side branch 166 either before or after the balloons 121, 122 are inflated depending on the nature of the procedure being performed and/or the preferences of an operator or physician.

In some implementations and/or procedures, the guide wire that was inserted into the first branch of the bifurcation to facilitate the original positioning of the catheter may be withdrawn to the proximal side of the opening 116 and then advanced into the opening so that the same guide wire is used to enter the main and side branches of the bifurcation. In other implementations and/or procedures, different guide wires may be used so that a first guide wire may be left in place in the first (e.g. main) branch 163 while the second guide wire is being positioned in the second (e.g. side) branch 166. In still other implementations and/or procedures, the first guide wire may be withdrawn fully from the vessel and the second guide wire introduced in its place by passing the second guide wire through the guide wire lumen 104 and out the opening 116. Of course, the first branch that is entered may be either the main branch or the side branch of a bifurcation.

Figure 12:
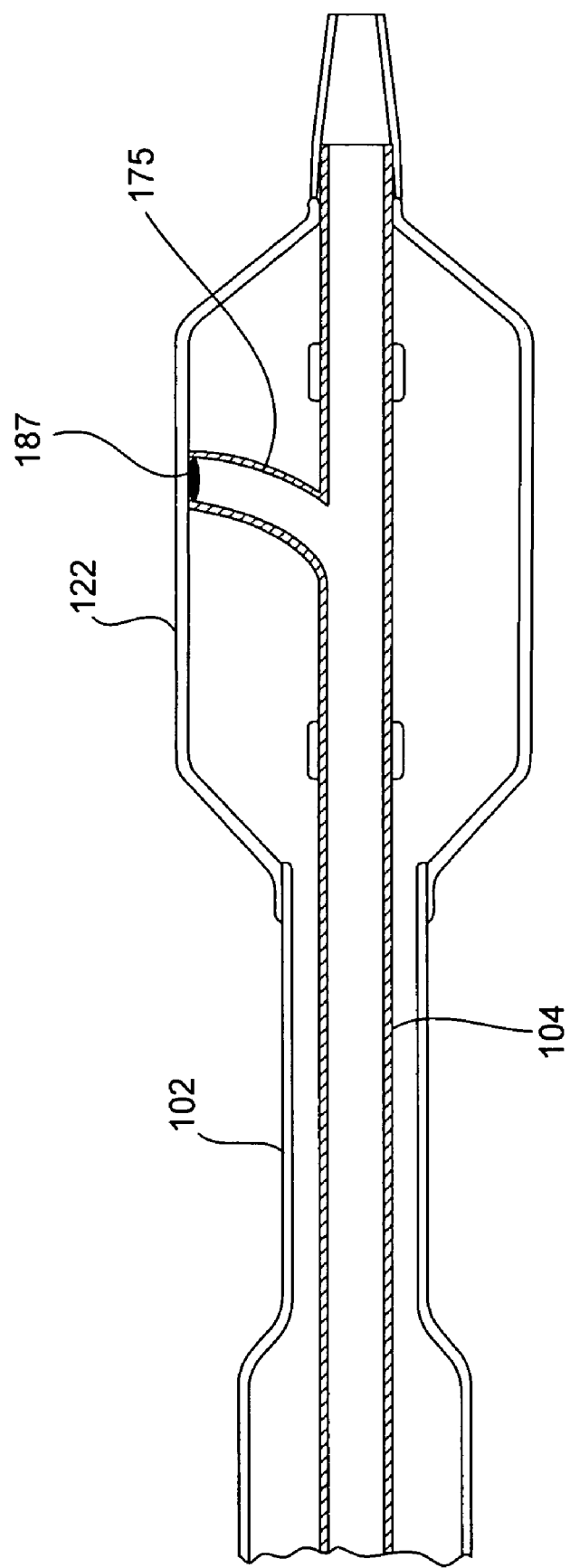
FIG. 12 is a diagrammatic cross sectional side view of a device with a guide in accordance with another embodiment of the present invention.

Referring next to FIG. 12, another embodiment will be described. In this embodiment, a guide 175 is provided adjacent the opening 116. The guide, which may take the form of a guide wire tube, extends laterally from the base structure and effectively forms a channel between the balloons. The guide is arranged so that when a guide wire passes through the opening 116 it enters the guide 175. Such a guide arrangement may be used to better control the angle at which the guide wire leaves the catheter and is particularly useful when it is desirable to direct the guide wire in a direction that forms a relatively large angle relative to the longitudinal axis of the catheter. Of course, in embodiments that have multiple openings 116 in the guide tube segment, multiple guides 175 may be provided. If a guide is used, it is generally desirable that the guide not extend laterally beyond the folded balloons when the catheter is originally inserted into the vessel. This can readily be accomplished via a variety of mechanisms including folding the guide tube(s) under the balloon or adhering the guide tube to the balloon. With these arrangements, the guide tube would move into place when the balloon is inflated. A similar purpose can also be accomplished by providing a relatively short guide segment that does not extend above the folded height of the balloons. This type of approach is particularly useful when it is desirable to insert the lateral guide wire before the balloons are inflated.

In still other embodiments, the guide channel can be formed simply by adhering a lumen between the adjoining portions of the balloons or adhering adjoining portions of the balloons together in a manner that forms a channel over the opening. For example, adjacent portions of the balloon segments may be attached to define the guide channel using adhesives, welding or similar processes. In other embodiments, the guide channel may be formed by adding a pair of longitudinally spaced apart sleeves over the inflatable member to define the channel. In this arrangement, the gap between the sleeves effectively defines the channel. Alternatively, the channel may be formed from a separate piece or as an extension of a guide wire lumen. The guide may be formed in a wide variety of other ways as well.

Figure 13:
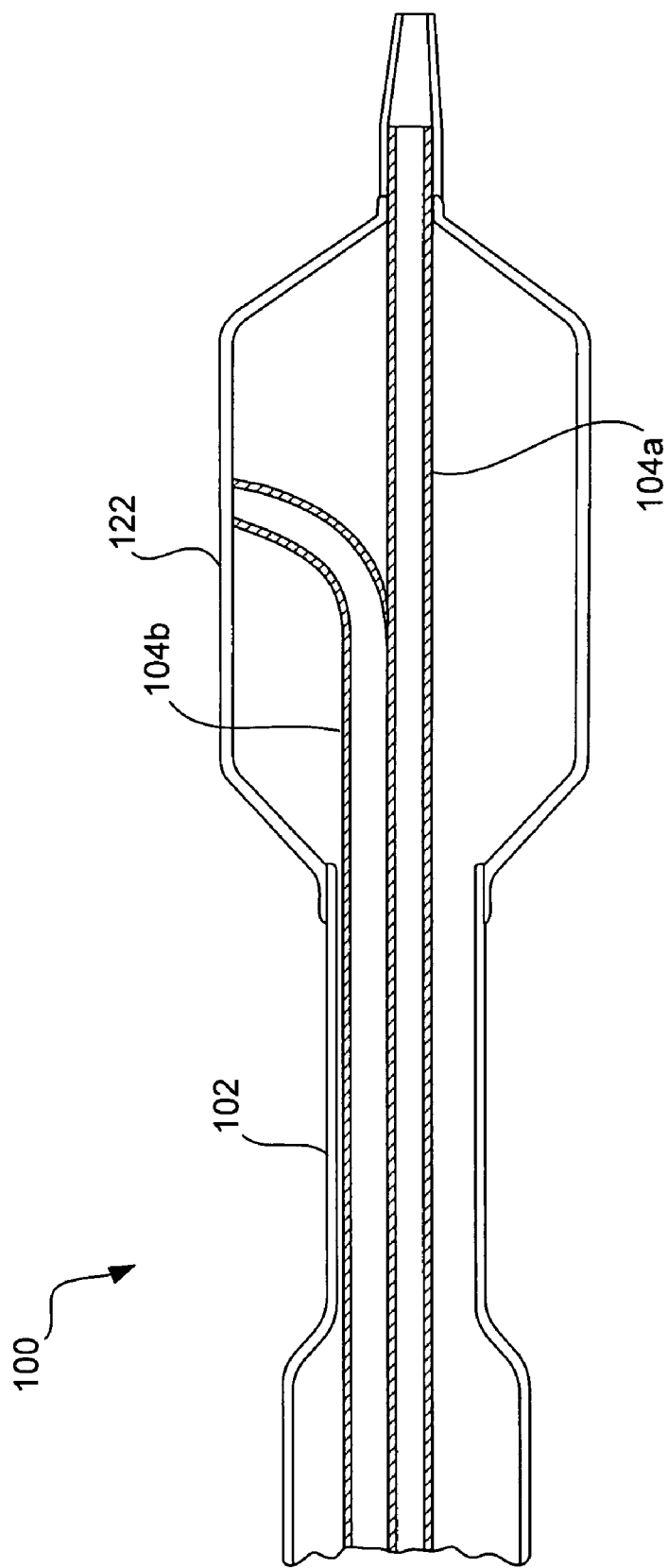
FIG. 13 is a diagrammatic side view of another embodiment of the invention, which utilizes a tubular member having a pair of guide wire lumens.

As suggested above, in many applications it may be desirable to utilize two guide wires during a procedure. The need for two guide wires may be a function of the particular device being used, the procedure being performed or simply a matter of surgeon preferences. In such applications, it may be desirable to include a pair of guide wire lumens 104(*a*), 104(*b*) in the flexible tubular member as best illustrated in FIG. 13. With this arrangement, one of the guide wire lumens 104(*a*) may open at the distal end of the flexible tubular member. Typically, this guide wire lumen would not include any side openings and would be used in conjunction with a guide wire inserted into the main branch of the vessel. The second guide wire lumen 104(*b*) opens to the side of the catheter. In a preferred embodiment, the distal end of the second guide wire lumen 104(*b*) is curved and extends through adjoining portions of the inflatable members 121, 122 thereby forming a guide channel that directs the guide wire to the desired location. However, in other embodiments, the guide channel may be formed in other manners as previously described or a simple side opening could be provided in the second guide wire lumen.

In some embodiment the first guide wire lumen 104(*a*) ends distal to the distal end of the inflatable members. In other embodiments the guide wire lumen may end exactly at the distal end of at least one of the inflatable members. In still other embodiments, the first guide wire lumen will end proximal to the distal end of the inflatable member and the inflatable member (or a structure carried by the inflatable member) therefore forms the distal end of the catheter.

The second guide wire lumen 104(*b*) can be a lumen that is integrally formed as part of the flexible tubular member 102. Alternatively the second guide wire lumen 104(*b*) may be a lumen that is pushed or drawn through the center guide wire lumen 104(*a*) or another suitable lumen in the flexible member such that the second guide wire lumen 104(*b*) exits laterally between the 2 balloons. The purpose of this embodiment is to apply maximal support to the guide wire as it enters the vessel branch located to the side of the balloons. This type of arrangement is particularly useful when the bifurcation angle is greater than approximately 60 degrees. In such an arrangement additional support is helpful to direct the guide wire towards the entrance of the branch to be entered. With the described arrangement, the guide wire is directed laterally as it exits the catheter, which makes it particularly suitable for directing the guide wire into a side branch of a vessel bifurcation.

In still other embodiments, the second guide wire lumen 104(*b*) may open into a guide channel that curves or extends laterally in the region of the inflation structure. As suggested above in the earlier described embodiments, the guide channel may be formed in different ways. By way of example, as previously described, the channel may be formed by attaching portions of the balloon together by using methods like adhesives, welding or adding a sleeve over the two portions of the inflatable member to define the channel. Alternatively, the channel may be formed from a separate piece or as an extension of a second guide wire lumen.

In some embodiments the second guide wire lumen will end distal to the distal end of the inflatable members. In other embodiments the guide wire lumen will end exactly at the distal end of at least one of the inflatable members. In a further embodiment the second guide wire lumen will end proximal to the distal end of the inflatable member and the inflatable member will form the distal end of the catheter. A first guide wire lumen will extend laterally from the base structure. The guide wire lumen may be formed in different ways. By way of example, the channel may be formed by attaching portions of the balloon segments together by using methods like adhesives, welding or adding a sleeve over the two portions of the inflatable member to define the channel. Alternatively, the channel may be formed from a separate piece or as an extension of a guide lumen.

As best illustrated in FIG. 13, a marker 187 may be provided at the distal end of the second guide wire lumen to help facilitate positioning the opening 116 (and thus the second guide wire) at a desired location. Similar markers may be utilized in the guides 175 utilized in the embodiment illustrated in FIG. 12 or any of the other described guide channel structures.

The described structures may be used in a wide variety of applications, including applications such as angioplasty and stent delivery in the vicinity of a vessel bifurcation. As pointed out above, in many stent delivery (and angioplasty) applications it is preferable that the expansion of the inflatable structure 120 be generally uniform in all directions. This can be difficult when two unconstrained balloons are used as balloons 121 and 122. Therefore, in many applications it will be desirable to utilize a sheath or other appropriate structure to help constrain the balloons. By way of example, FIG. 9 illustrates an inflatable structure 120 that includes a pair of tubular sleeves (sheaths) 126 that are positioned on opposite sides of the opening 116. The sleeves 126 help constrain the balloons 121 and 122 so that the entire inflatable structure 120 maintains a more cylindrical shape. In other embodiments a third balloon segment (not shown) that surrounds the distal end of the balloons 121, 122 may be used as the sheath. In such embodiments, one or both ends of the third (outer) balloon would typically be cut off to facilitate sliding it over the balloons 121 and 122. Accordingly, the third balloon would not itself be inflated since it must have an opening that is sized appropriately for the guide wire to pass through as it exits the inflatable structure 120. Rather, the third balloon is simply intended to constrain the first and second balloons 121, 122 in a manner that imparts a more cylindrical shape to the entire inflatable structure 120.

A variety of other techniques, including various balloon fabrication techniques may be used to help the inflation balloons 121, 122 attain their desired shape. For example, the balloons may be formed into an approximate D-shape during balloon forming.

Figure 14:
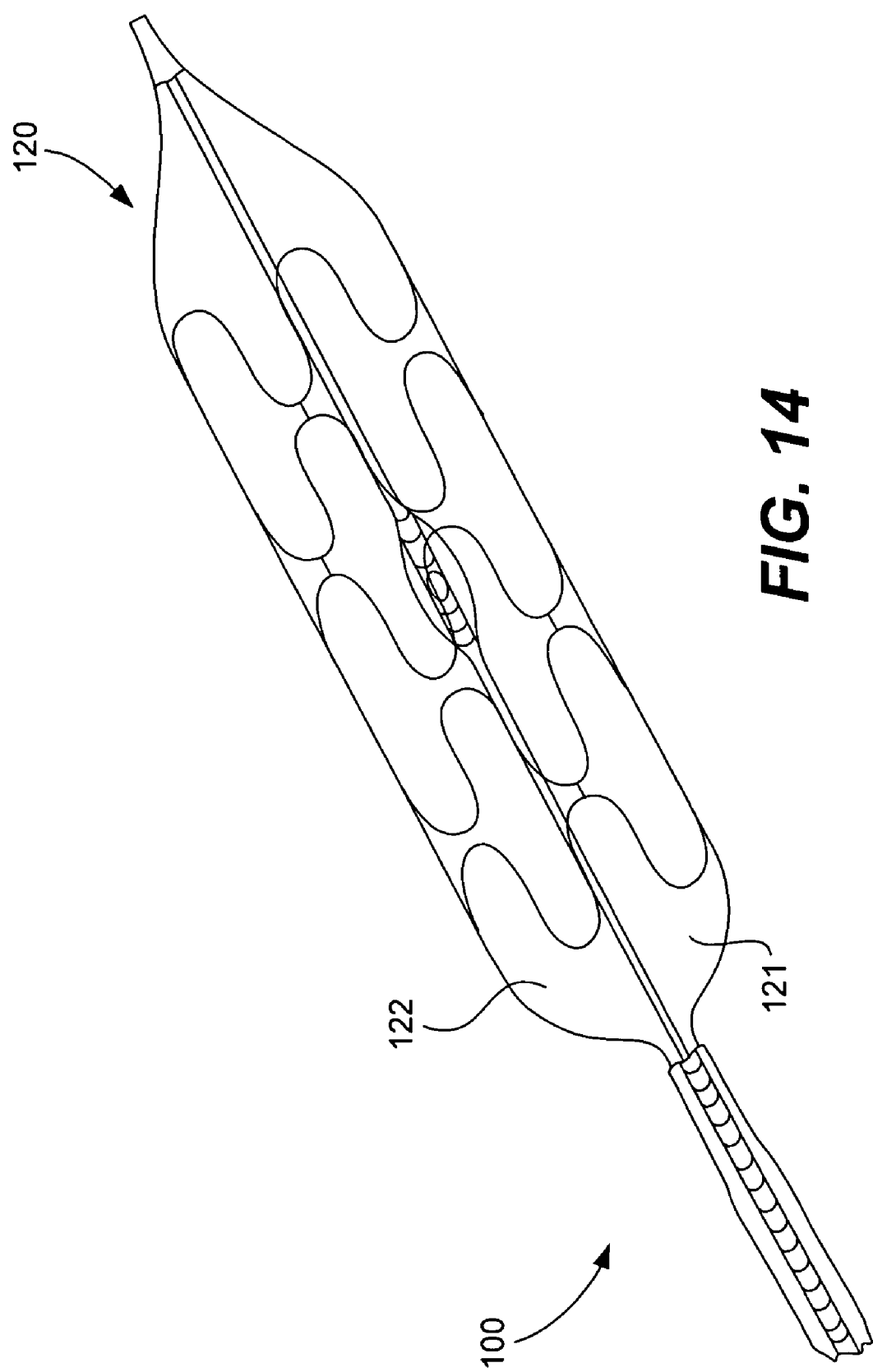
FIG. 14 is a stent delivery catheter incorporating a side access port in accordance with another embodiment of the invention.

It should be appreciated that the described catheter arrangement can be useful in a wide variety of interventional procedures. For example, it may be useful in applying stents to one or both branches of a vessel bifurcation. By way of example, a representative stent delivery catheter is illustrated in FIG. 14. Alternatively, the described arrangements may be useful in facilitating appropriate diagnostic or treatment procedures in a branch of a bifurcation, either together with or separate from a procedure that might be performed in the main branch. The side branch procedures may include such procedures as angioplasty procedures, atherectomy procedures, stent delivery procedures, localized drug delivery procedure, visualization procedures, tissue or fluid (e.g., blood) sample acquiring procedures, etc.

Although only a few embodiments of the invention have been described in detail, it should be appreciated that the invention may be implemented in many other forms without departing from the spirit or scope of the invention. Although the side access port (opening) has been described primarily in the context of permitting a guide wire to pass there through into a side branch of a bifurcation, it should be appreciated that a variety of small sized tools may be passed through the side access port in addition to or in place of a guide wire. The described structure may be incorporated into a simple angioplasty or stent delivery catheter or into different and/or more complicated medical devices. Therefore, the present embodiments are to be considered as illustrative and not restrictive and the invention is not to be limited to the details given herein, but may be modified within the scope and equivalents of the appended claims.

What is claimed is:

1. A catheter comprising:
    an elongate flexible tubular member having a plurality of lumens including a guide lumen, the flexible tubular member being sized suitably for insertion in a body vessel;
    an inflatable structure carried by a distal portion of the flexible tubular member, the inflatable structure including at least first and second inflation members, wherein said inflation members are maintained in an abutting side-by-side orientation relative to one another and about said guide lumen, each inflation member being in fluid communication with an associated fluid supply lumen; and
    wherein the inflatable structure further includes an opening that communicates with the guide lumen and opens on a side portion of the catheter in a gap between the first and second inflatable members, whereby a distal end of a guide wire may be advanced through the guide lumen and out of the opening such that the guide wire passes radially between the first and second inflatable members.

2. A catheter as recited in claim 1 wherein the inflatable structure includes a base structure that is part of the flexible tubular member and wherein the opening is in the base structure.

3. A catheter as recited in claim 2 wherein the inflatable structure further comprises a channel that is arranged to extend laterally from the base structure in a region between the first and second inflatable members when the inflatable members are in an inflated position, the channel including the opening and being arranged to communicate with the guide lumen.

4. A catheter as recited in claim 3 wherein the inflatable members are balloons and the channel is formed by adhering portions of the balloons together to define the channel.

5. A catheter as recited in claim 2 wherein the inflatable members are independent balloons that are each attached to the base structure by an adhesive.

6. A catheter as recited in claim 1 wherein:
    the flexible tubular member includes a second guide lumen that opens substantially distally at a distal end of the catheter; and
    the distal end of the first guide lumen is curved to extend laterally in a region between the first and second inflatable members when the inflatable members are in an inflated position.

7. A catheter as recited in claim 1 further comprising a retaining sheath that surrounds and constrains at least a portion of the inflatable members.

8. A catheter as recited in claim 1 wherein the first and second inflation members are both in fluid communication with the same fluid supply lumen.

9. A catheter as recited in claim 1 wherein the first and second inflation members are in fluid communication with separate fluid supply lumens.

\* \* \* \* \*